(12) United States Patent
Raptis

(10) Patent No.: US 6,596,259 B1
(45) Date of Patent: Jul. 22, 2003

(54) METAL BASED CUBANE STRUCTURE CONTAINED IN AN OCTANUCLEAR COMPLEX STABLE OVER SEVERAL OXIDATION STATES AND A METHOD OF PRODUCING THE SAME

(75) Inventor: Raphael G. Raptis, Rio Piedras, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 09/470,504

(22) Filed: Dec. 22, 1999

Related U.S. Application Data

(60) Provisional application No. 60/113,537, filed on Dec. 22, 1998.

(51) Int. Cl.$^7$ .................. A61B 5/055; A61K 51/00; A61K 49/00; A61K 49/04; A61M 36/14; C07D 233/00; C07D 233/02

(52) U.S. Cl. .................. 424/9.32; 424/1.65; 424/9.1; 424/9.3; 424/9.4; 424/9.42; 548/300.1

(58) Field of Search .................. 424/1.29, 9.32, 424/9.36, 9.42, 1.65, 9.1, 9.3, 9.4; 548/300.1

(56) References Cited

U.S. PATENT DOCUMENTS

| | | | |
|---|---|---|---|
| 4,385,174 A | | 5/1983 | Iqbal et al. |
| 4,730,064 A | * | 3/1988 | Halbert et al. .................. 556/15 |
| 5,141,855 A | | 8/1992 | Schmittou |
| 5,194,626 A | | 3/1993 | Rolf et al. |
| 5,364,953 A | * | 11/1994 | Beaty et al. .................. 556/46 |
| 5,482,699 A | | 1/1996 | Almen et al. |
| 5,554,357 A | | 9/1996 | Rajagopalan |
| 5,582,814 A | * | 12/1996 | Scott et al. .................. 424/9.364 |
| 5,614,168 A | * | 3/1997 | Berg et al. .................. 424/9.42 |
| 5,624,662 A | | 4/1997 | Unger et al. |
| 5,850,086 A | | 12/1998 | Que, Jr. et al. |
| 5,892,033 A | | 4/1999 | Komamura et al. |
| 5,932,190 A | * | 8/1999 | Almen et al. .................. 424/9.42 |

OTHER PUBLICATIONS

Stuart L. James, D. Michael P. Mingos, Andrew J.P. White and David J. Willilams. Anion–templated formation of a unique inorganic 'super–adamantoid' cage [Ag$_6$(triphos)$_4$(O$_{33}$SCF$_3$)4]$^{2+}$[triphos=(PPh$_2$CH$_2$)$_3$CMe]— *Chem. Commun.*, 1998. Pp. 2323–2324. London, UK.

Raphael G. Raptis, Irene P. Georgakaki, David C.R. Hockless; *Angew. Chem. Int. Ed.*, 38, No. 11, pp. 1632–1634 (1999).

Mario V. Capparelli, Paul Hodge, Brian Piggott; *Chem. Commun.*, pp. 937–938 (1997).

Sergiu M. Gorun, Stephen J. Lippard; *Inorganic Chemistry*, vol. 30, No. 7, pp. 1625–1630 (1991).

F. Albert Cotton, L.M. Daniela, L.R. Falvello, J.H. Matonic, C.A. Murillo, X. Wang, H. Zhou; *Inorganica Chimica Acta* 266, pp. 91–102 (1997).

Vinod S. Nair, Karl S. Hagen; *Inorg. Chem.*, vol. 31, pp. 4048–4050 (1992).

Wolfgang Micklitz, Stephen J. Lippard; *J. Am. Chem. Soc.*, 111, pp. 6856–6858 (1989).

Katerina Dimitrou, Jui–Sui Sun, Kirsten Folting, George Christou; *Inorg. Chem.*, 34, pp. 4160–4166 (1995).

F. Albert Cotton, Stan A. Duraj, Wiewlaw J. Roth; *Inorg. Chem.*, 23, pp. 4042–4045 (1984).

Martin K. Ehlert, Steven J. Rettig, Alan Storr, Robert C. Thompson, James Trotter; *Acta Cryst.*, C50, pp. 1023–1026 (1994).

Steven C. Shoner, Phillip P. Power; *Inorg. Chem.*, 31, pp. 1001–1010 (1992).

Kingsley L. Taft, Andrea Caneschi, Laura E. Pence, Christopher D. Delfs, Georgia C. Papaefthymiou, Stephen J. Lippard; *J. Am. Chem. Soc.*, 115, pp. 11753–11766 (1993).

Kingsley L. Taft, Georgia C. Papaefthymiou, Stephen J. Lippard; *Science*, vol. 259, pp. 1302–1305 (Feb. 1993).

Kingsley L. Taft, Georgia C. Papaefthymiou, Stephen J. Lippard; *Inorg. Chem.*, 33, pp. 1510–1520 (1994).

Helmut Beinert, Richard H. Holm, Eckard Munck; *Science*, vol. 277, 1, pp. 653–659 (Aug. 1997).

Michael W. Willer, Jeffrey R. Long, Craig C. McLauchlan, R.H. Holm; *Inorganic Chemistry*, vol. 27, No. 2, pp. 328–333 (1998).

O.M. Yaghi, Z. Sun, D.A. Richardson, T.L. Groy; *J. Am. Chem. Soc.*, 116, pp. 807–808 (1994).

George M. Whitesides, John P. Mathias, Christopher T. Seto; *Science*, vol. 254, pp. 1312–1319 (Nov. 1991).

* cited by examiner

Primary Examiner—Russell Travers
Assistant Examiner—Lauren Q. Wells
(74) Attorney, Agent, or Firm—Patent Law Offices of Heath W. Hoglund

(57) ABSTRACT

The present invention is directed to a complex comprising a redox-active metal cluster in a chemically inert shell. The inventive complex has the formula $M_8(\mu^4-E)_4(\mu-L)_{12}X$, where M is chosen from a transition metal, a lanthanide, an actinide and mixtures thereof; E is a chalcogenide; L is a bridging ligand; and X is a terminal ligand. The chemically inert shell enables the complex to exhibit structural stability over several oxidation states, and to exhibit reversible electrochemical reduction properties. A single reactor method of making this complex from simple starting materials is also disclosed. The active center further allows the octanuclear complex to be used in making supercluster assemblies that have electron transfer properties or in making contrasting agents for MRI applications, for example.

6 Claims, 4 Drawing Sheets

METAL BASED CUBANE STRUCTURE CONTAINED IN AN OCTANUCLEAR COMPLEX STABLE OVER SEVERAL OXIDATION STATES AND A METHOD OF PRODUCING THE SAME

This application claims priority under 35 U.S.C. §120 to U.S. provisional application serial No. 60/113,537, filed Dec. 22, 1998.

This invention relates to a metal-based cubane structure contained in an octanuclear complex which can be used as an electron transfer agent. More specifically, this invention is directed to a redox-active metal-based structure, protected inside an inert coating. This complex, which can be defined as $M_8(\mu^4\text{-}E)_4(\mu\text{-}L)_{12}X_4$, is stable over several oxidation states. The present invention is also directed to a method of making this product from simple starting materials.

Thermodynamic stability is a desired property of materials to be used in most commercial applications. At the same time, however, chemical versatility is typically required for the manifestation of interesting properties or catalytic activity. A combination of these contrasting characteristics is typically achieved by the coating of large surfaces or particles with inert substances, at the macroscopic and microscopic scale, respectively. Such structures are known to naturally occur at the macromolecular level when, for example, metal active centers are protected inside the organic part of metalloproteins.

The complex encompassed by the present invention has a core, which is the source of redox properties, encapsulated in a protective shell. Such a complex provides an ideal building block for the construction of one-, two-, and three-dimensional materials. These materials can be constructed by connecting or bonding units of the complex made in accordance with the present invention by bridging atoms or groups. The bridges can be either bidentate ligands, which replace terminal atoms, or bifunctional substituents, which connect the units through substitution at the 3-, 4- or 5-position of their respective pyrazoles. The advantage of using the inventive complex for the construction of these materials, instead of a single metal atom, or other mono- or polynuclear products, is that the complex can withstand redox manipulation without significant geometrical changes, which would cause the structure of the material to collapse. The inventor has discovered that the structural integrity of the present complex is a function of the way it is composed. Specifically, the desired redox properties are a function of the metal core, while the connections required for the construction of the above proposed materials take place at the outer inert shell.

Accordingly, construction of the 1-, 2-, and 3-dimensional materials leaves the core unaffected. Similarly, redox changes in the core leave the outer structure unaffected. In addition, when the metal atoms employed are paramagnetic, the complexes encompassed in the invention are also paramagnetic, or can become paramagnetic in one of their oxidation states. The materials which will be prepared from the inventive complex will have all the magnetic and redox properties of this building unit, possibly even amplified.

The inventor has surprisingly and unexpectedly discovered that by encapsulating a redox active core inside an inert protective coating, the resulting material retains structural stability over several oxidation states. This result is achieved by separating the center of redox activity, the core, from the outer surface of the molecule, the coating. In some cases, the molecular symmetry of the complexes $M_8(\mu^4\text{-}E)_4(\mu\text{-}L)_{12}X_4$ allows the existence of optically active forms, which can be prepared as racemic mixtures or enantiomerically enriched or enantiomerically pure forms.

SUMMARY OF THE INVENTION

To achieve the beneficial properties of stability and versatility previously described, the present invention is directed to molecules having an active center coated with inert substances. More specifically, the present invention is directed to a complex comprising redox-active metal clusters protected inside a chemically inert shell. The invention is also directed to the generation of four additional forms of the complex through electrochemical reduction of the inventive complex. In addition, the present invention is directed to methods of using these structures as building blocks for the construction of durable supercluster assemblies having electron-transfer properties. The invention is further directed to uses of this complex as a dopant in materials, i.e., polymers to impart magnetic or electrical properties to the doped material. The inventive complex may also be used as a contrast agent in magnetic resonance imaging (MRI) applications, for example.

Pyrazolates are convenient bridging ligands or complexing agents for the synthesis of polynuclear products in which, due to the aromatic character of the ligand or complexing agent, the chemical activity is restricted to the metal centers.

The present invention is directed to a material represented by formula (I)

$$M_8(\mu^4\text{-}E)_4(\mu\text{-}L)_{12}X_4 \qquad (1)$$

where M is one or more transition metals, a lanthanide, an actinide and M is in the +2, +3, or +4 oxidation state, or two different oxidation states. Preferably, M is $Fe^{3+}$, $Mn^{3+}$ or $Co^{3+}$;

$\mu$ represents a bridging group, i.e., a bridging ligand or a bridging chalcogenide;

E is a chalcogenide, preferably O, S or Se;

L is a bridging ligand such as a pyrazole, or a pyrazole substituted at any or all of the 3-, 4-, or 5-positions;

X is a terminal ligand, such as Cl, Br or an alkyl group.

The inventive complex can be in a racemic, an enantiomerically-enriched or an enantiomerically-pure form.

More preferably, formula (I) represents a Fe III-complex designated as

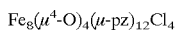

$$Fe_8(\mu^4\text{-}O)_4(\mu\text{-}pz)_{12}Cl_4$$

wherein pz represents a pyrazolato anion, $C_3H_3N_2$, and $\mu$ represents a bridging group, i.e., a bridging pz, or a bridging atom, such as an oxygen atom. The Fe (III) complex optionally has T-symmetry.

The inventor has unexpectedly discovered that the inventive Fe III complex contains a redox-active $Fe_4O_4$ core, protected inside a Fe-pyrazolate coating, which is stable over five oxidation states. The $Fe_4O_4$-core of the Fe (III) complex is the first example of an all-ferric/oxygen cubane complex. Consistent with the +3 valence of this Fe III complex are the shorter Fe-O bonds of formula (I), i.e., 2.040(4) Å average, compared to those of its lower-valence analogues.

As stated, the inventor has also discovered that the complex defined by formula (I) is stable over several, preferably five, oxidation states. Stability is defined as the ability of the complex of formula (I) to retain the structure and stoichiometry of its neutral form when it is reduced by one, two, three or four, one-electron processes. In other words, the inventor has discovered that the species represented by (I), (I)$^{-1}$, (I)$^{-2}$, (I)$^{-3}$ and (I)$^{-4}$ are thermodynamically stable under the electrochemical reduction of the complex of formula (I).

The inventor has also discovered that manipulation of the solubility of the inventive complex is possible through substitution at the outer shell. This can be done through substitution at either the positions of the chlorine atoms, or the 3-, 4-, or 5-position of the pyrazoles. While the preferred form of the complex is hydrophobic, i.e., insoluble in water, but soluble in a large number of organic solvents, it can easily become water soluble by attaching hydrophilic groups to its surface through such substitutions. Water-soluble derivatives of the inventive complex may find medicinal use, either in therapeutic or diagnostic applications, for example, as MRI contrast enhancing agents.

The inventive complex, when manipulated in the above stated manner to make it water soluble, allows the complex to be used in a method of generating an image of a mammal. Such a method comprises administering to a mammal, in an amount effective to provide an image, a contrast agent comprising the complex of formula (I).

Additionally, the inventor has discovered that the complex defined by formula (I) can be assembled in a single reactor from simple starting materials that are commercially available.

DETAILED DESCRIPTION OF THE INVENTION

Preparation of a Fe III Complex

Figure 1:
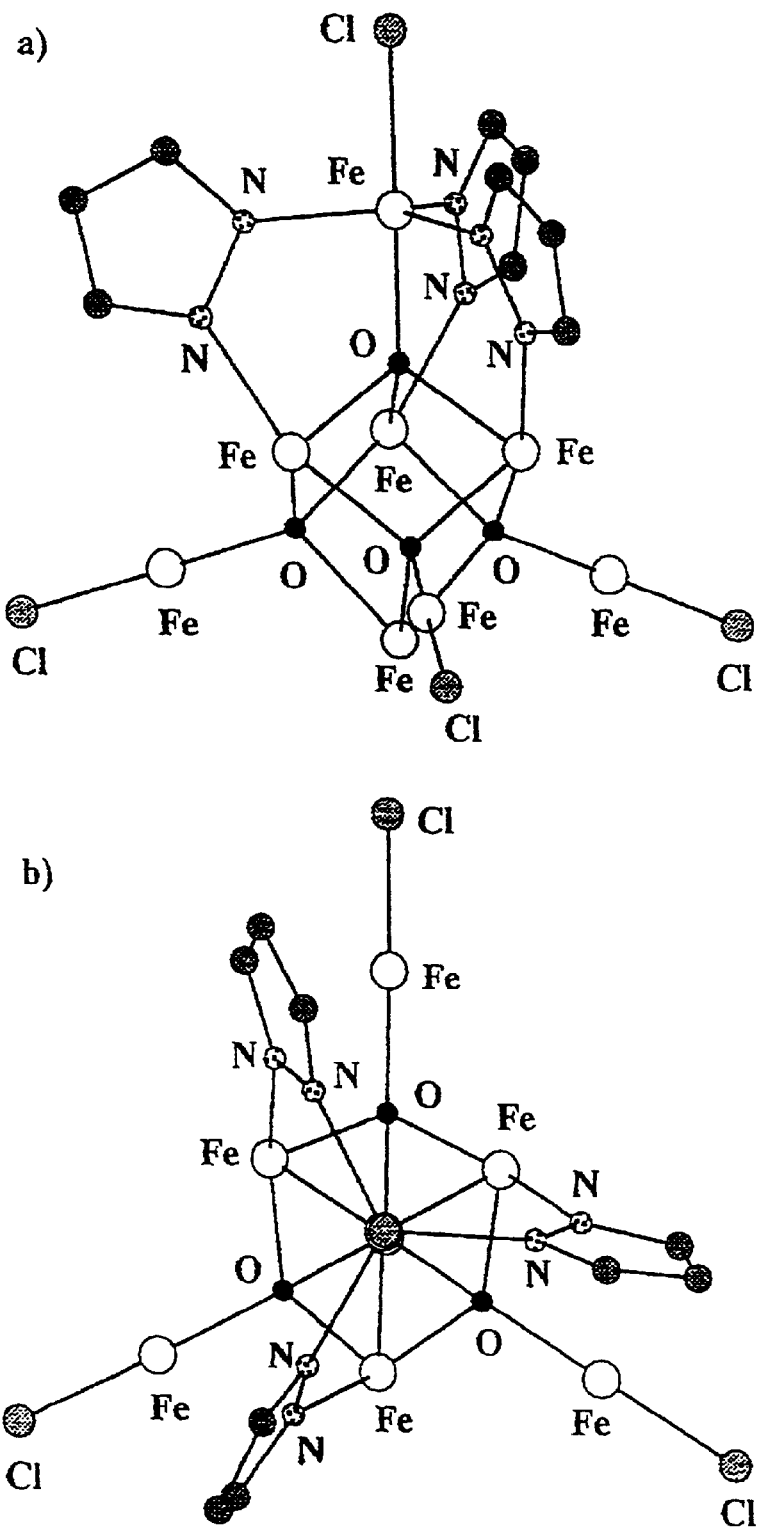
FIG. 1a) illustrates a side view of the $Fe_8O_4Cl_4$ part of a complex of formula (I), and of three of the twelve pyrazolato groups therein.
FIG. 1b) illustrates the same as 1a), but is viewed down a $C_3$-axis.

The starting materials that can be used to prepare the $Fe_8(\mu^4-O)_4(\mu-pz)_{12}Cl_4$ complex defined by formula (I) include the following commercially available materials: anhydrous ferric chloride ($FeCl_3$), pyrazole ($C_3H_4N_2$, pzH), and 3,5-dimethylpyrazole ($C_5H_8N_2$, 3,5-Me$_2$-pzH). Also, sodium pyrazolate (Na-pz), or potassium pyrazolate (K-pz) can be readily prepared from pyrazole and sodium hydride or potassium hydride. Either pyrazolate works equally well. Other common reagents can be used as pyrazolate-transfer agents in the preparation of formula (I).

In a typical preparation of a complex of formula (I), an ordinary reaction flask is charged with the starting materials, and a solvent under an inert atmosphere, such as $N_2$ or Ar. The flask is closed while the reaction proceeds. After about 1 hour, the reaction is completed and the flask is opened to the laboratory atmosphere. A pyrazolate is then added and the reaction flask is kept open for at least 24 hours. The reaction mixture is not placed under inert atmosphere again. Once the solvent volume is reduced to approximately ⅓ of its initial volume, a hydrocarbon such as hexane is added to precipitate a complex of formula (I) as an impure microcrystalline solid. The complex solid can be further purified using standard chromatographic techniques.

The invention is illustrated in greater detail in the following, non-limiting example.

EXAMPLE

Preparation

In a standard reaction flask, 3,5-Me$_2$pzH (0.375 g, 3.90 mmol) was mixed with $FeCl_3$ (0.180 g, 1.11 mmol) in 15 ml $CH_2Cl_2$ under $N_2$. The flask was then closed. After about 1 hour, the flask was opened and K-pz (0.355 g, 3.30 mmol) was then added to the mixture, which product was exposed to an ambient environment for several days. A crystalline product of formula (I) was subsequently prepared by mixing the $CH_2Cl_2$ solution of formula (I) with hexane. The slow mixing of $CH_2Cl_2$ and hexane, along with gradual evaporation of the mixture, resulted in well formed dark-red crystals of formula (I). Specifically, the dark-red, air-stable complex defined by formula (I) was precipitated by the addition of hexane after the $CH_2Cl_2$ solvent was reduced to a volume of approximately 5 ml. The above reaction yielded greater than 30% of a complex of formula (I).

Analysis of Resulting Precipitated Crystals

The larger crystals made according to the example were used for a single crystal X-ray structure determination, while the smaller ones were used for all other analyses. Analyses performed on the crystals grown from the $CH_2Cl_2$/hexane solution of formula (I) produced the following results.

A. Elemental Properties

The precipitated crystals exhibited a melting point of approximately 565 K, as determined by DTA analysis. The analyses for C, H, N, and Cl were performed gravimetrically by an elemental analyzer. The analysis for Fe was done by Atomic Absorption spectroscopy (flame atomization). The analyses of all five elements show the w/w % of the element in a sample of formula (I)-½ hexane. The first number reported is the measured weight percent of the element, averaged from duplicate runs, while the second number is the theoretically calculated value for formula (I)-½ hexane. The fact that the measured value is so close to the theoretical value evidences the correctness of the characterization given below:

Results:

C=31.14 (31.19),

H=2.81 (2.87),

N=21.59 (22.39),

Cl=9.62 (9.45),

Fe=29.43 (29.76).

B. Spectroscopic Properties

1. Electronic spectroscopy: The electronic spectrum of formula (I) in a $CH_2Cl_2$ solution, recorded in the UV/Vis/NIR region, revealed a $\lambda_{max}$=359 nm, consistent with the red color of the material.

2. Infrared spectroscopy: A powdered sample of formula (I) formed into a KBr pellet showed the following IR absorption peaks (where the peak intensity was denoted as vs=very strong, s=strong, m=medium and w=weak) in cm$^{-1}$, using a KBr disk: 1490 m, 1417 m, 1362 s, 1268 s, 1169 s, 1145 m, 1078 w, 1045 vs, 963 w, 915 w, 894 w, 763 s, 615 m, 555 m and 476 s. With a polyethelene pellet of formula (I), three additional IR absorption peaks were observed at 349 s, 331 s, and 308 s.

3. Mass spectroscopy: The mass spectrum of formula (I) was recorded by the Fast Atom Bombardment technique and the following m/z peaks were observed (the fragment to which they are attributed in parenthesis): 1457.6 (M+), 1420.6(M-Cl+), 1388.5(M-pz+), 1353.6(M-Cl,pz+), 1321.5 (M-2pz+), 1286.5(M-2pz,Cl+).

C. Magnetic Properties

Magnetic moment: $u_{eff}$=6.52 B.M., calculated from a Faraday balance susceptibility measurement at 290 K.

D. Crystallographic Properties

Red parallelepiped crystals appropriate for X-ray diffraction study were grown from the $CH_2Cl_2$/hexane solution of formula (I). A Rigaku-A-FC6S diffractometer employing a Mo–K$\alpha$=0.71069 Å beam source showed the following cell parameters for the primitive triclinic cell, $P\bar{1}$(No.2), characteristic of the crystals (with the standard deviation in parenthesis): a=12.367(5), b=12.508(5), c=20.794(4) Å, $\alpha$=77.45(3), $\beta$=80.80(3), $\gamma$=70.27(3)°, V=2942(2) Å$^3$, Z=2, $d_{calc}$=1.694 g/cm, $\mu$=21.53 cm$^{-1}$.

FIG. 1 illustrates the crystal structure for the $Fe_4O_4$-cube. Specifically, the bond lengths were found to be (with the standard deviation in parenthesis): Fe—O=2.022(4)–2.056(4) Å; Fe—Fe=3.059(1)–3.088(1) Å; Fe—N=2.048(5)–2.070(5) Å; Fe—O—Fe=97.1(2)–98.7(2) Å; O—Fe—O= 81.1(2)–82.4(1) Å; For the outer Fe—atoms: Fe—O=1.944(4)–1.963(4) Å; Fe—Cl=2.267(2)–2.276(2) Å; Fe—N= 2.007(5)–2.025(5) Å; N—Fe—N=114.2(2)–124.6(2)°; Fe—N—N=119.1(4)–121.6(4)°.

The crystallographic characterization of formula (I) was performed using well-established procedures. In analyzing the crystal structure data, corrections were made for Lorentz and polarization effects using an empirical absorption factor based on azimuthal scans, which resulted in a reliability factor of R=0.036, and a goodness-of-fit indicator of 1.73.

The eight Fe-atoms associated with formula (I) were located on $C_3$-axes at positions defining two concentric tetrahedra with average Fe—Fe edges of 3.074(2) and 5.853(4)°, respectively. The $\mu^4$-O atoms, which connected the eight-Fe-atom network, were expected to be efficient mediators of antiferromagnetic coupling and expected to account for the relatively low effective magnetic moment of 6.52 B.M. of formula (I). Within each ($\mu^4$-O)Fe$_4$ group, the O-atoms were displaced from the centers towards the bases of the Fe$_4$-trigonal pyramids.

Figure 2:
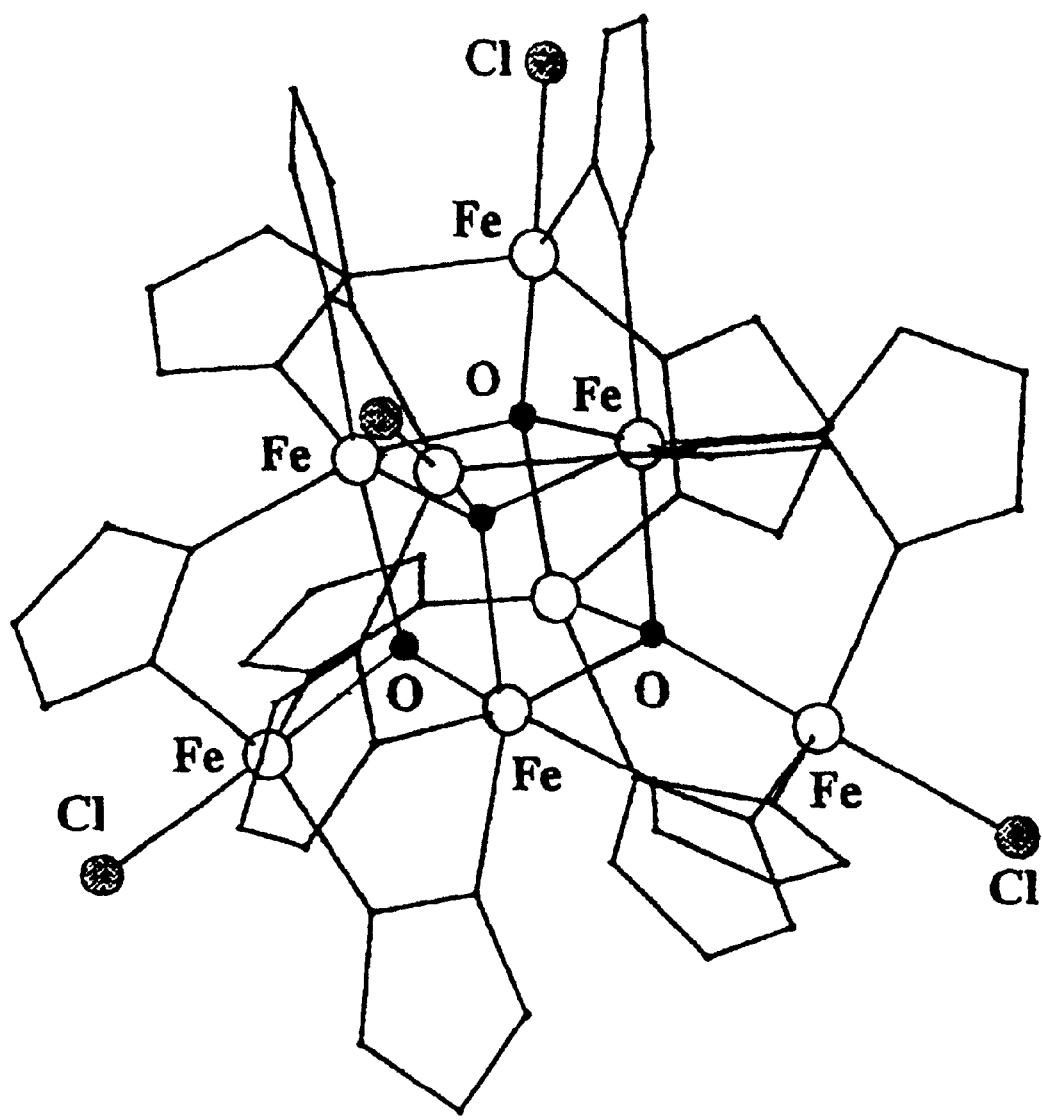
FIG. 2 illustrates the structure of a complex of formula (I) comprising spherical atoms of arbitrary radii. Hydrogen atoms are not shown.

While the $Fe_8O_4Cl_4$ skeleton of formula (I) was in tetrahedral arrangement, the propeller-like rotation of the $\mu$-pz groups eliminated the mirror planes of $T_d$ symmetry, thus reducing the overall symmetry of formula (I) to that of the T-point group. A consequence of this symmetry was that formula (I) occurred in two enantiomeric forms; first co-crystallized as a racemic mixture (i.e., a 50/50 mixture of the two possible enantiomeric forms), the interconversion of which requires the rearrangement of all twelve pyrazolato bridges by simultaneous rotation about the four $C_3$-axes of 1. The arrangement of twelve pyrazole rings in the outer part of formula (I) gave this molecule an approximate appearance of a sphere of approximately 12 Å diameter and a hydrophobic surface responsible for its high solubility in non-polar solvents (FIG. 2). FIG. 2 shows one enantiomeric form, while the other form is its mirror image.

E. Electrochemical Properties

Figure 3:
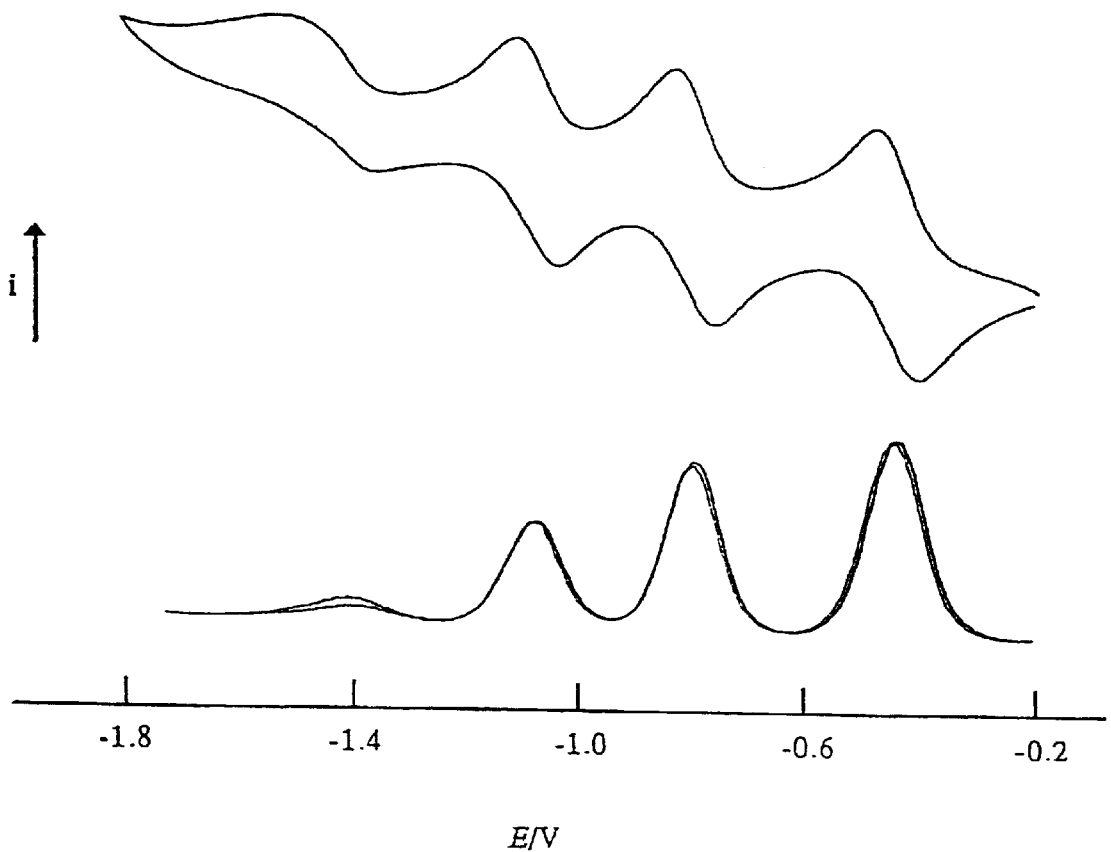
FIG. 3 illustrates voltammetry of a complex of formula (I) in 0.1 M $Bu_4NPF_6$/PrCN, with a scan speed=100 mV/sec, T=223 K, Pt-disk working electrode, versus Fc/Fc+, wherein a) represents a cyclic voltammogram, and b) represents a cyclic AC-scan.
Figure 4:
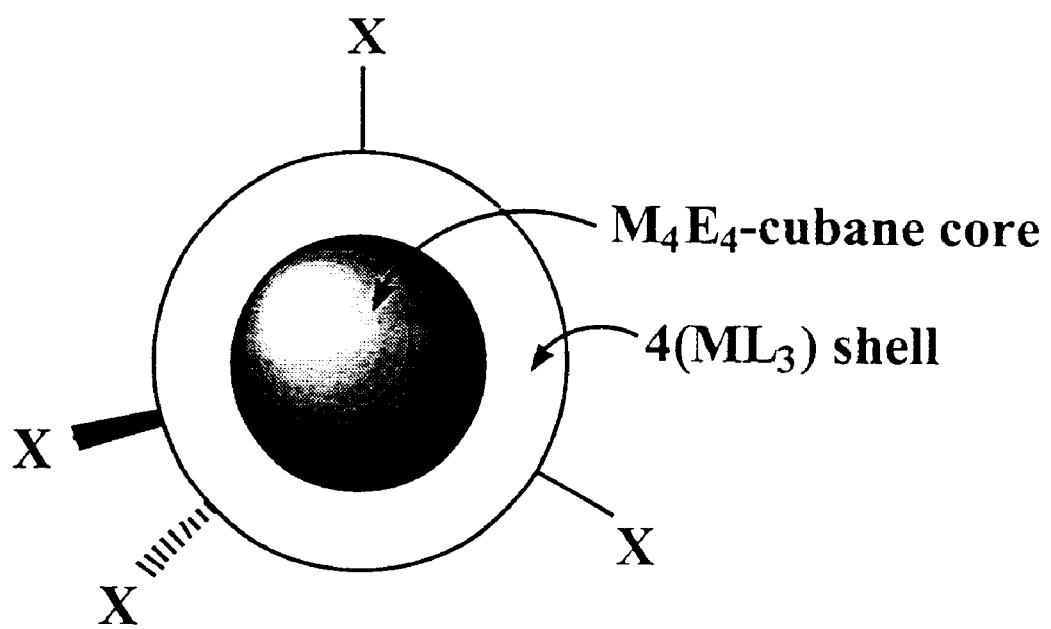
FIG. 4 illustrates an octanuclear complex containing a metal cubane core in an inert shell.

The electrochemical properties of the complex of the invention were studied by Cyclic and AC Voltammetric techniques, in $CH_2Cl_2$ solvent, 0.5 M terabutylammonium hexafluorophosphate supporting electrolyte, in a voltammetric cell with the standard three-electrode configuration, employing a platinum working electrode. The electrochemical study, from −2.00 to +2.20 V, showed three reversible reductions at −0.43, −0.78, and −1.07 V vs. Fc/Fc+. A fourth reduction at −1.38 V was irreversible at 285 K, but became chemically reversible and electrochemically quasi-reversible in chilled solution. (FIG. 3).

As no oxidation was observed, it was evident that the complex of formula (I) retained its structural integrity, in its neutral or some anionic form, over the measured 4.20 V window, i.e., −2.00 to +2.20 V. The complete electrochemical reversibility of the first three reductions, at ambient or low temperature, indicated that no significant structural rearrangement accompanied those electron-transfer processes. The unusual stability of formula (I) over five oxidation states can be accounted for by the encapsulation of the $Fe_4O_4$-core inside the outer shell of four interlocked Fe($\mu^4$-pz)$_3$Cl groups forcing its structural integrity, in a fashion similar to the wrapping of apoferritin around the Fe/O cluster of ferritin. The spontaneous assembly from mononuclear precursors, as well as the stability and rich electrochemistry of formula (I), indicate the likelihood of developing an electron-transfer protein based on a $Fe_4O_4$ active center described in formula (I).

The four tetrahedrally arranged chlorine atoms at the outer shell of formula (I) were readily substituted by anionic or neutral ligands in simple metathesis reactions providing a convenient means by which to manipulate the size and solubility of the octanuclear cluster, as well as to connect octanuclear units by bridging ligands into covalent supramolecular assemblies. Such derivatives of formula (I) retained the redox characteristics of their parent compound with minimal variations of the $E_{1/2}$ values. These results indicate that the $Fe_4O_4$-core was the site of the redox activity.

What is claimed is:

1. A Fe (III) complex comprising a redox-active metal cluster in a chemically inert shell, said complex having the formula $$Fe_8(\mu^4\text{-O})_4(\mu\text{-pz})_{12}Cl_4 \qquad (I)$$

wherein $\mu$ is a bridging group, and pz is a pyrazolato anion, wherein said redox active metal cluster comprises a $Fe_4O_4$ cubane core which is stable over five oxidation states, and further wherein said chemically inert shell comprises four iron atoms and twelve pyrazolato groups.

2. The Fe (III) complex of claim 1, wherein said pyrazolato anion is $C_3H_3N_2$.

3. The Fe (III) complex of claim 1, which has T-symmetry.

4. A method for making the Fe (III) complex of claim 1, wherein the starting materials are mixed in a single reactor.

5. A process for producing reduced forms of the Fe (III)-complex of claim 1, wherein said reduced forms comprise (I)$^{1-}$, (I)$^{2-}$, (I)$^{3-}$, or (I)$^{4-}$, said process comprising electrochemically reducing said complex $Fe_8(\mu^4\text{-O})_4$ $(\mu\text{-pz})_{12}Cl_4$.

6. A contrast agent comprising the Fe (III)-complex of claim 1.